US012629056B2

(12) United States Patent
Hao et al.

(10) Patent No.: US 12,629,056 B2
(45) Date of Patent: May 19, 2026

(54) MICRODIALYSIS SYSTEM COMPRISING FLOW FEEDBACK DEVICE

(71) Applicant: Shanghai Coloshore Automation Technology Co., Ltd., Shanghai (CN)

(72) Inventors: Xiangyi Hao, Shanghai (CN); Yunhong Zhang, Shanghai (CN)

(73) Assignee: SHANGHAI COLOSHORE AUTOMATION TECHNOLOGY CO., LTD., Shanghai (CN)

( * ) Notice: Subject to any disclaimer, the term of this patent is extended or adjusted under 35 U.S.C. 154(b) by 331 days.

(21) Appl. No.: 18/287,629

(22) PCT Filed: Apr. 18, 2022

(86) PCT No.: PCT/CN2022/087508
§ 371 (c)(1),
(2) Date: Oct. 19, 2023

(87) PCT Pub. No.: WO2022/222898
PCT Pub. Date: Oct. 27, 2022

(65) Prior Publication Data
US 2024/0181143 A1      Jun. 6, 2024

(30) Foreign Application Priority Data

Apr. 22, 2021    (CN) .......................... 202110433208.2

(51) Int. Cl.
*A61B 5/145*          (2006.01)
*B01D 61/24*          (2006.01)
*A61M 1/16*           (2006.01)
(52) U.S. Cl.
CPC ....... *A61B 5/14525* (2013.01); *A61M 1/1615* (2014.02); *A61M 1/1643* (2014.02); *A61M 2205/3334* (2013.01); *B01D 61/243* (2013.01)

(58) Field of Classification Search
CPC .............. A61M 1/1615; A61M 1/1643; A61M 2205/3334; A61M 1/1601; A61M 1/1621;
(Continued)

(56) References Cited

U.S. PATENT DOCUMENTS 6,780,322 B1 *   8/2004   Bissler ................ A61M 1/3437
                                                          604/4.01
2002/0082490 A1    6/2002   Roeper et al.
(Continued)

FOREIGN PATENT DOCUMENTS

CN          1163576 A      10/1997
CN        101703817 A       5/2010
(Continued)

OTHER PUBLICATIONS

International Search Report and Written Opinion issued Jul. 19, 2022 in PCT/CN2022/087508.
(Continued)

*Primary Examiner* — Susan S Su
(74) *Attorney, Agent, or Firm* — Panitch Schwarze Belisario & Nadel LLP

(57)                    ABSTRACT

A microdialysis system includes: an input device, first and second connecting pipelines and a flow feedback device that includes a connecting needle, a liquid collecting tank, a calibration weighing module, and a flow feedback control display module; the weighing module weighs the liquid in the liquid collecting tank regularly according to conditions and a program set in the display module and transmits a measured liquid weighing value to the display module; the display module performs a difference operation between the current liquid weighing value and the previous liquid weighing value to obtain a weighing sampling difference value, compares the weighing sampling difference value with a preset value to monitor whether the connecting needle
(Continued)

Liquid external joint 451
452
42
433
431
432
434
46
430 outputs liquid normally, and further feeds back a flow state of fluid in the first and second connecting pipelines. In the microdialysis system, the flow state of each connecting pipeline is monitored by weighing the collected liquid.

10 Claims, 6 Drawing Sheets

(58) Field of Classification Search
CPC .............. A61M 1/1647; A61M 1/1654; A61M 1/1656; A61M 2202/0413; A61M 2205/3331; A61M 2205/3379; A61M 2205/583; B01D 61/243; B01D 2311/14; B01D 2311/16; B01D 61/28; B01D 61/32; A61B 5/14525
See application file for complete search history.

(56) References Cited

U.S. PATENT DOCUMENTS

| | | | |
|---|---|---|---|
| 2007/0191702 | A1 | 8/2007 | Yodfat et al. |
| 2007/0276328 | A1* | 11/2007 | Childers ................. A61M 1/80 |
| | | | 604/131 |

FOREIGN PATENT DOCUMENTS

| | | |
|---|---|---|
| CN | 102014739 A | 4/2011 |
| CN | 108992725 A | 12/2018 |
| CN | 109357738 A | 2/2019 |
| CN | 109771720 A | 5/2019 |
| CN | 110426107 A | 11/2019 |
| CN | 111712196 A | 9/2020 |
| CN | 112972803 A | 6/2021 |
| EP | 0403394 A1 | 12/1990 |

OTHER PUBLICATIONS

Office Action issued Jun. 29, 2021 in Chinese Application No. 202110433208.2.

* cited by examiner

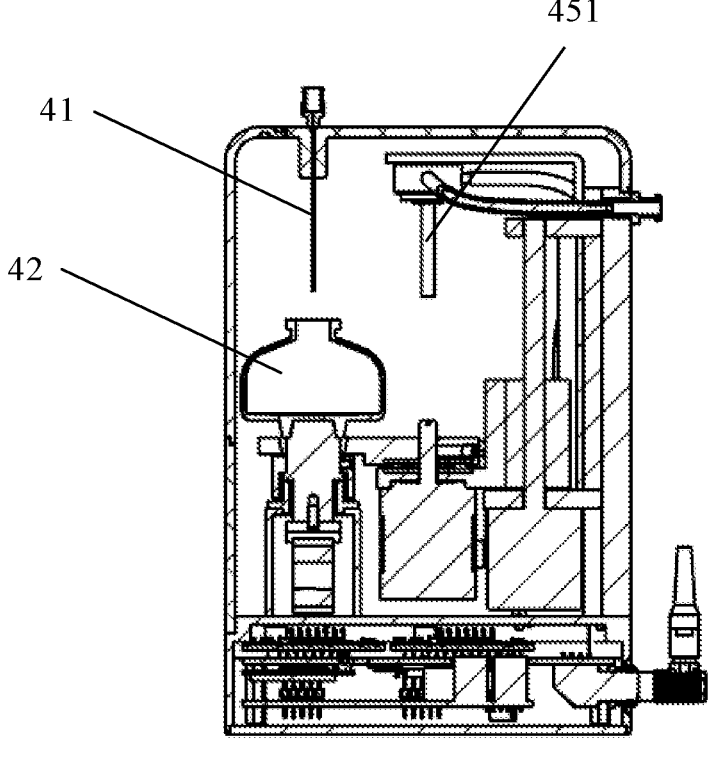
FIG    6

MICRODIALYSIS SYSTEM COMPRISING FLOW FEEDBACK DEVICE

CROSS-REFERENCE TO RELATED APPLICATIONS

This application is a Section 371 of International Application No PCT/CN2022/087508, filed Apr. 18, 2022, which was published in the Chinese language on Oct. 27, 2022, under International Publication No. WO 2022/222898 A1, which claims priority under 35 U.S.C. § 119(b) to Chinese Application No. 202110433208.2 filed Apr. 22, 2021, the disclosures of each of which are incorporated herein by reference.

TECHNICAL FIELD

The present invention relates to the field of medical equipment and in particular to a microdialysis system including flow rate feedback device.

BACKGROUND

Due to the fact that many microdialysis experiments/treatments require long-term dialysis (several hours or more), and some require online analysis and monitoring of collected dialysate, the following situations often occur during microdialysis experiments/treatments: (1) clogging of microdialysis probes or connecting pipelines; (2) leakage of liquid and air from connecting pipelines; (3) if the syringe is not positioned properly, a timely monitoring, judgment, and alarm device is needed to assist in the experiment/treatment to ensure the normal operation of the entire connecting pipelines and supporting devices.

However, in existing conveying pipelines, there is no sensor or equipment that can accurately measure the flow rate inside the pipeline in real-time in the current technology. In addition, after chemical analysis of a dialysate, especially after some dialysate combined with online analysis devices reacting, the dialysate often contains toxic and harmful substances that require non-contact liquid collection and treatment.

Therefore, there is an urgent need to develop a microdialysis system comprising a flow rate feedback device in this field flow rate feedback device which can monitor the flow status of the connecting pipelines of the microdialysis system by weighing the collected liquid, and the system integrates liquid collection and automatic drainage functions.

SUMMARY

The purpose of the present invention is to provide a microdialysis system comprising a flow rate feedback device. The microdialysis system can monitor the flow status of the connecting pipelines of the microdialysis system by weighing the collected liquid, and the system integrates liquid collection and automatic drainage functions.

The present invention provides a microdialysis system comprising a flow rate feedback device.

The microdialysis system comprises a perfusion device, a first connecting pipeline, a second connecting pipeline, and the flow rate feedback device. The flow rate feedback device comprises a connecting needle, a liquid collection container, a calibration weighing module, and a flow rate feedback control display module.

Wherein, the perfusion device comprises a micropump and a syringe, and the micropump pumps dialyzable substances into the first connecting pipeline through the syringe.

One end of the first connecting pipeline is fluidly connected to the syringe, and the other end of the first connecting pipeline is fluidly connected to an inlet of a microdialysis probe. The first connecting pipeline is configured to transport dialyzable substances to the microdialysis probe, so that the dialyzable substances enter the living organism through the microdialysis probe.

The second connecting pipeline is configured to transport dialysate from the living organism to the flow rate feedback device. One end of the second connecting pipeline is fluidly connected to an outlet of the microdialysis probe, and the other end of the second connecting pipeline is fluidly connected to the connecting needle.

The liquid collection container is provided below the connecting needle and configured to collect dialysate from the living organism.

The calibration weighing module is configured to regularly measure the weight of a liquid in the liquid collection container according to conditions and programs set in the flow rate feedback control display module, and transmit a measured liquid weighing value to the flow rate feedback control display module.

The flow rate feedback control display module performs a difference operation between a current liquid weighing value and a previous liquid weighing value to obtain a weighing sampling difference, and compares the weighing sampling difference with a predetermined value to monitor whether the connecting needle is discharging liquid normally, and thus gives a feedback on a state of flow rate of the liquid in the first connecting pipeline and the second connecting pipeline.

In another preferred embodiment, the dialysate from the living organism is selected from the following group: the dialysate from a living organism that has undergone microdialysis, a liquid formed by a biochemical reaction of the dialysate, or a combination thereof.

In another preferred embodiment, the flow rate feedback control display module further comprises a display screen, which is configured to display the current liquid weighing value and the weighing sampling difference for users to monitor liquid weight changes.

In another preferred embodiment, the flow rate feedback control display module of the flow rate feedback device may also comprise an alarm module, which sends an alarm signal to the users when the weighing sampling difference is not equal to the predetermined value.

In another preferred embodiment, the calibration weighing module performs automatic calibration before weighing the dialysate collected in the liquid collection container.

In another preferred embodiment, the calibration weighing module comprises a stage, a pressure sensor, a lifting mechanism and a rotating motor. The pressure sensor and the rotating motor are provided below the stage, and the lifting mechanism is provided at the side of the stage.

In another preferred embodiment, the calibration weighing module includes a stage, which includes a first section and a second section. The liquid collection container is provided at the first section, and a customized weight(s) are provided at the second section.

In another preferred embodiment, the stage is an L-shaped stage.

In another preferred embodiment, the calibration weighing module further comprises a pressure sensor provided below the stage.

In another preferred embodiment, when the calibration weighing module is performing a weighing, the pressure sensor is provided directly below the first section of the stage; when the calibration weighing module is performing a calibrating, the pressure sensor is provided directly below the second section of the stage.

In another preferred embodiment, the pressure sensor is connected to a scale, and when the calibration weighing module is automatically calibrated, the liquid collection container is separated from the scale.

In another preferred embodiment, the calibration weighing module further comprises a lifting mechanism which includes a lifting motor and a lead screw. The lifting mechanism drives the stage to move away from or close to the pressure sensor in a vertical direction.

In another preferred embodiment, the lead screw is connected to the stage, and the lifting motor is connected to the lead screw.

In another preferred embodiment, the calibration weighing module further comprises a rotating motor connected to the stage, the rotating motor is configured to drive the stage to rotate in a horizontal plane.

In another preferred embodiment, the calibration weighing module further comprises a rotating motor, the rotating motor cooperates with the lifting mechanism to switch between the liquid collection container and the customized weights on the pressure sensor, achieving the weighing of the liquid in the liquid collection container and the calibration with the customized weights.

In another preferred embodiment, the pressure sensor is connected to a scale, which includes scale head.

The first section of the stage is provided with a first through hole, and the bottom of the liquid collection container is provided with a collection container annular projection. The collection container annular projection passes through the first through hole and there is a certain gap between the collection container annular projection and the first through hole. When the calibration weighing module performs weighing, the scale head is embedded in the collection container annular projection.

In another preferred embodiment, the liquid collection container comprises mouth and body, wherein the collection container annular projection is provided at the bottom of the body, and the diameter of the mouth is much smaller than the diameter of the body.

In another preferred embodiment, the second section is provided with a second through hole, and the bottom of the customized weight is provided with a weight annular projection. The weight annular projection passes through the second through hole and there is a certain gap between the weight annular projection and the second through hole. When the calibration weighing module performs calibrating, the scale head is embedded in the weight annular projection.

In another preferred embodiment, when the calibration weighing module performs calibrating, the lifting mechanism lifts the stage in the vertical direction to allow the liquid collection container to detach from the scale head, and then the rotating motor rotates the stage so that the second section of the stage is located above the pressure sensor. Then, the flow rate feedback control display module automatically zeros the pressure sensor, then, the lifting mechanism drives the stage to descend in the vertical direction to the weight annular projection of the customized weight embedded in the scale head (i.e., the scale supports the customized weight, and the pressure sensor transmits the measured signal to the flow rate feedback control display module, so that the flow rate feedback control display module completes calibration according to internal instructions.

In another preferred embodiment, upon completion of calibration, the calibration weighing module performs weighing, and the lifting mechanism lifts the stage in the vertical direction to detach the customized weight from the scale head. Next, the rotating motor rotates the stage so that the first section of the stage is located above the pressure sensor, and the flow rate feedback control display module automatically zeros the pressure sensor, then, the lifting mechanism drives the stage to descend in the vertical direction until the collection container annular projection is embedded in the scale head (i.e., the scale supports the liquid collection container), and the pressure sensor transmits the measured signal to the flow rate feedback control display module. The measured signal is processed and displayed on the display screen of the flow rate feedback control display module.

In another preferred embodiment, the flow rate feedback control display module includes a signal processor and a controller.

In another preferred embodiment, the signal processor is used to convert the voltage signal generated by the pressure sensor from an analog quantity to a digital quantity. The signal processor simultaneously receives commands from the controller and executes various commands such as clearing (reset to zero), calibrating, and reading pressure sensor signals. The controller is used to control an action(s) of the lifting mechanism and the rotating motor of the calibration weighing module.

In another preferred embodiment, the flow rate feedback control display module includes an upper computer for calculating, displaying of sampled values modifying parameters, alarming, etc.

In another preferred embodiment, the calibration weighing module further comprises a pressure sensor, which performs weighing through a connected scale. When the stage is raised and the scale is empty, the flow rate feedback control display module will make the pressure sensor automatically reset to zero. When the stage is lowered, the scale is embedded with the collection container annular projection of the liquid collection container and supports the liquid collection container, at this time, the through hole of the stage forms a completely separated gap from the scale and the bottom of liquid collection container. At this time, the flow rate feedback control display module will process the signal of the pressure sensor and the corresponding data is displayed on the display screen.

In another preferred embodiment, the bottom of the customized weight also has a weight annular projection. When the stage is raised and the scale is empty, the flow rate feedback control display module make the pressure sensor automatically reset to zero. When the stage is lowered, the scale is embedded in the customized weight annular projection to support the customized weight. At this time, the through hole of the stage forms a completely separated gap from the scale and the bottom of the customized weight, the signal processor of the flow rate feedback control display module receives the signal data of the pressure sensor, and completes calibration according to the instructions of the controller.

In another preferred embodiment, the flow rate feedback device further comprises a cover, wherein the connecting needle is provided on the cover, the liquid collection container and the calibration weighing module are provided inside the cover.

In another preferred embodiment, the flow rate feedback device further comprises an automatic drainage mechanism, which is used to discharge the liquid in the liquid collection container.

In another preferred embodiment, the flow rate feedback device further comprises a base, wherein the liquid collection container, the calibration weighing module, and the automatic drainage mechanism are provided above the base.

In another preferred embodiment, the flow rate feedback device is portable.

In another preferred embodiment, in order to compact the flow rate feedback device, the signal processor and the controller are provided in the base.

In another preferred embodiment, the automatic drainage mechanism includes a drain pump and a drain pipe. When the weighing value of the liquid in the liquid collection container reaches the maximum preset threshold, the flow rate feedback control display module will coordinate the lifting mechanism with the rotating motor to insert the drain pipe into the liquid collection container, and start the discharge pump to discharge the liquid from the liquid collection container.

In another preferred embodiment, the automatic drainage mechanism operates independently of the calibration weighing module.

In another preferred embodiment, the weighing accuracy of the calibration weighing module is within the range of ±0.003 g.

In another preferred embodiment, the micropump has a speed of 0.05 uL/min-30 uL/min through a designated syringe and connecting pipeline.

In another preferred embodiment, the calibration weighing module can set a timed weighing interval based on the flow rate.

In another preferred embodiment, the calibration weighing module is used to calibrate the calibration weighing module before entering the weighing program based on the conditions and procedures set in the flow rate feedback control display module.

In another preferred embodiment, the flow rate feedback control display module can perform parameter setting and action control of the calibration weighing module and the automatic drainage mechanism.

In another preferred embodiment, the connecting needle, the first and the second connecting pipelines, and the syringe are all disposable in a medical environment.

In another preferred embodiment, the microdialysis system further comprises other connecting pipelines.

It should be understood that within the scope of the present invention, the above-mentioned technical features of the present invention and the specific technical features described below (according to the embodiments) can be combined with each other to form new or preferred technical solutions. Due to space limitations, it will not go into detail here.

DESCRIPTION OF THE DRAWINGS

In order to explain the embodiments of the present invention or the technical solutions in the prior art more clearly, the drawings needed to be used in the description of the embodiments or prior art are briefly introduced hereinafter. It should be understood that the drawings in the following description are only some implementation examples of the present invention. Ordinary technical personnel in this field can also obtain other implementation examples based on these drawings without inventiveness work.

FIG. 6 is a structural schematic diagram of the A-A section in FIG. 5.

Figure 1:
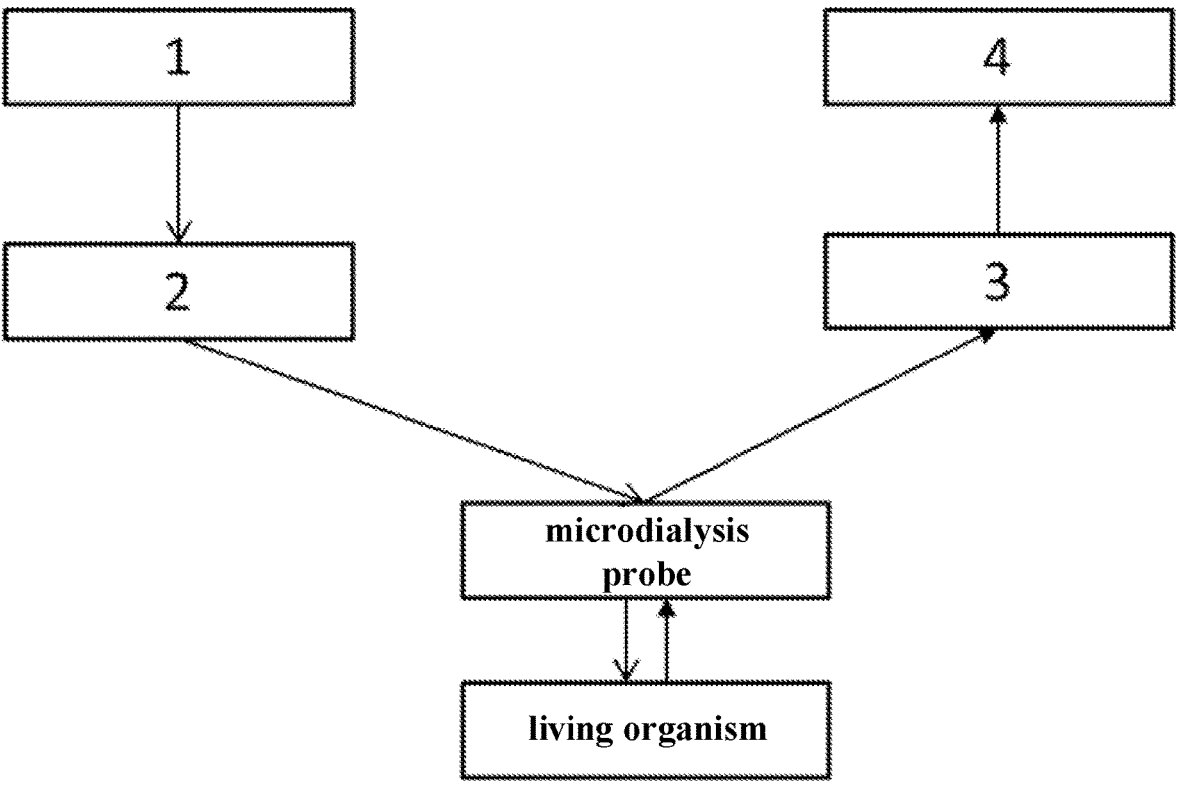
FIG. 1 is a schematic diagram of a microdialysis system including a flow rate feedback device according to the present invention.

In each attached drawings, the markings are as follows:

1—Perfusion device
2—First connecting pipeline
3—Second connecting pipeline
4—Flow rate feedback device
40—Cover
41—Connecting needle
42—Liquid collection container
43—Calibration weighing module
430—Stage
431—Customized weight
432—Pressure sensor
433—Lifting mechanism
434—Rotating motor
44—Flow rate feedback control display module
45—Automatic drainage mechanism
451—Drain pipe
452—Drain pump
453—Drain joint
46—Base

DETAILED DESCRIPTION

Based on extensive and in-depth research, the inventors have discovered a microdialysis system that includes a flow rate feedback device for the first time. By regularly weighing and measuring the liquid collection container of the flow rate feedback device at the end of the microdialysis system pipeline, the flow status of the first and second connecting pipelines of the microdialysis system is monitored by analyzing and calculating the obtained weighting data, so that the problems of changes in flow rate can be found timely in a short period of time. Then, the following faults can be analyzed and determined: (1) whether the microdialysis probe or connecting pipeline is blocked; (2) whether there is any liquid or air leakage in the connecting pipeline; (3) whether the syringe is not mounted properly, etc. The flow rate feedback device also includes a display screen, which allows users to view the flow trend chart of the micro-flow pipeline through monitoring the screen to determine the relative stable state of the pipeline. The flow rate feedback device further integrates an automatic drainage mechanism to pump the liquid in the liquid collection container into an external liquid bag/container when the liquid reaches the maximum preset threshold.

Terms

As used herein, the terms "weighing value" and "weighing sampling value" are interchangeable;

It should be noted that in the disclosure documents of this application, relational terms such as first and second are only used to distinguish one entity or operation from another entity or operation, and do not necessarily require or imply any actual relationship or order between these entities or operations. Moreover, the terms "comprising", "including", or any other variation thereof are intended to encompass non-exclusive inclusion, such that a process, method, item, or device that includes a series of elements not only includes those elements, but also other elements that are not explicitly listed, or also include elements inherent in such a process, method, item, or device. Without further limitations, the element limited by the statement 'comprising a' does not exclude the existence of another identical element in the process, method, item, or device that includes the element. In the disclosure documents of this application, if it is mentioned that a certain act is performed based on a certain element, it means that at least the act is performed based on that element, which includes two situations: only performing the act based on that element, and performing the act based on that element and other elements. Multiple and/or more expressions include 2 and more than 2 or more.

Flow Rate Feedback Device

In the present disclosure, a flow rate feedback device 4 with a unique structure is provided, which comprises a cover 40, a connecting needle 41, a liquid collection container 42, a calibration weighing module 43, a flow rate feedback control display module 44, and an automatic drainage mechanism 45. The rate flow rate feedback control display module 44 may comprises an alarm module.

The liquid collection container 42 is provided below the connecting needle 41 and is configured to collect dialysis liquid from a living organism; The calibration weighing module 43 is configured to regularly measure the weight of the liquid in the liquid collection container 42 according to the conditions and programs set in the flow rate feedback control display module 44, and transmit the measured liquid weighing value to the flow rate feedback control display module 44.

The flow rate feedback control display module 44 performs a subtract operation between the current liquid weighing value and the previous liquid weighing value to obtain a weighing sampling difference and compares it with the predetermined value to monitor whether the connecting needle 41 is discharging liquid normally, and then gives a feedback on the status/state of flow rate of the liquid in the first connecting pipeline 2 and the second connecting pipeline 3. When the weighing sampling difference is not equal to the predetermined value, the alarm module sends an alarm signal to the user.

Preferably, in order to make the flow rate feedback device compact and portable, the calibration weighing module 43 comprises a stage 430, a customized weight 431, a pressure sensor 432, a lifting mechanism 433, and a rotating motor 434. The pressure sensor 432 and the rotating motor 434 are arranged below the stage 430, and the lifting mechanism 433 is arranged on the side of the stage 430.

In an embodiment, the connecting needle 41 is provided on the cover 40 and connected to an outlet of the second connecting pipe. The liquid collection container 42, the calibration weighing module 43, and the automatic drainage mechanism 45 are all provided inside the cover 40, further preventing external air from entering the liquid collection container 42 and affecting the accuracy of the calibration weighing module.

In one embodiment, in a medical environment, the connecting needle 41, the first connecting pipeline 2, the second connecting pipeline 3, and the syringe are all disposable. In an embodiment, the size of the needle is usually selected based on the set liquid flow rate, and the principle is to ensure that the interval time for forming droplets can ensure that the calibration weighing module completes one weighing action. For example, G30 needle can be selected at a flow rate of 0.05-0.5 ul/min, G23 needle can be selected at a flow rate of 5 ul/min, and at higher flow rates, we can even make the tip of the needle that forms droplets into a larger plane to form larger droplets and ensure that the interval time between droplets is long enough.

Preferably, the flow rate feedback control display module 44 comprises a signal processor and a controller, and preferably, the flow rate feedback device 4 also comprises a base 46. The liquid collection container 42, calibration weighing module 43, and automatic drainage mechanism 45 are provided above the base 46. In order to make the flow rate feedback device compact, the signal processor and controller are provided in the base 46.

In the present disclosure, the liquid collection is carried out by a connecting needle at the end of the connecting pipeline, which collects a small amount of liquid in a non-contact state, and the droplet is collected into the liquid collection container by gravity. When the fluid flow automatic feedback system detects that the quality of the liquid in the liquid bottle reaches a limit value, the automatic drainage mechanism begins to work, and the liquid is pumped from the liquid collection container into the liquid bag/container. The liquid bag/container is regularly replaced by staff.

In the present disclosure, the state of fluid flow in the connecting pipeline is fed back based on whether the collected dialysate/liquid has increased in mass by a normal amount within a specified time, or whether its stagnation time is normal when no liquid is discharged (1 normal/2 blocked/3 leaking). After an alarm prompt, personnel intervene to check whether there is any abnormal phenomenon in the connecting pipeline and supporting equipment.

Microdialysis System Including Flow Rate Feedback Device

In the present disclosure, a microdialysis system including a flow rate feedback device is provided, which comprises an perfusion device 1, a first connecting pipeline 2, a second connecting pipeline 3, and a flow rate feedback device 4, wherein the perfusion device 1 includes a micropump and a syringe, and the micropump pumps the dialyzable substances through the syringe to the first connecting pipeline 2. One end of the first connecting pipeline 2 is fluidly connected to the syringe, the other end of the first connecting pipeline 2 is fluidly connected to the inlet of the microdialysis probe. The first connecting pipeline 2 is configured to transport the dialyzable substances to the microdialysis probe, so that the dialyzable substances enter the living organism through the microdialysis probe. The second connecting pipeline 3 is configured to transport dialysis fluid from the living organism to the flow rate feedback device 4. One end of the second connecting pipeline 3 is fluidly connected to the outlet of the microdialysis probe, and the other end of the second connecting pipeline 3 is fluidly connected to the flow rate feedback device 4.

In one embodiment, the dialysate from living organisms is selected from the following group: the dialysate from a living organism that has undergone microdialysis, the liquid formed by a biochemical reaction of the dialysate, or a combination thereof. In one embodiment, the micropump has a speed of 0.05 uL/min-30 uL/min through the specified syringe and connecting pipeline. In one embodiment, the microdialysis system also includes other connecting pipelines. In one embodiment, in a system with liquid (dialysate) generation, the second connecting pipeline can incorporate more connecting pipes before entering the flow rate feedback device, and the second connecting pipeline includes these incorporated connecting pipes.

In the following description, many technical details have been proposed in order to provide readers with a better understanding of the present disclosure. However, ordinary technical personnel in this art can understand that even without these technical details and various changes and modifications based on the following implementation methods, the technical solution claimed by the present disclosure can still be achieved.

Embodiment

Figure 2:
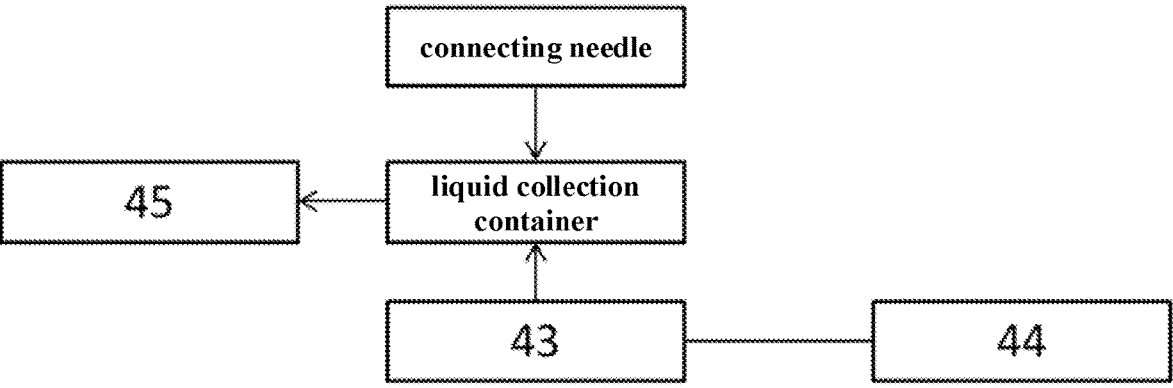
FIG. 2 is a schematic diagram of a portion of components of the flow rate feedback device according to the present invention.
Figure 3:
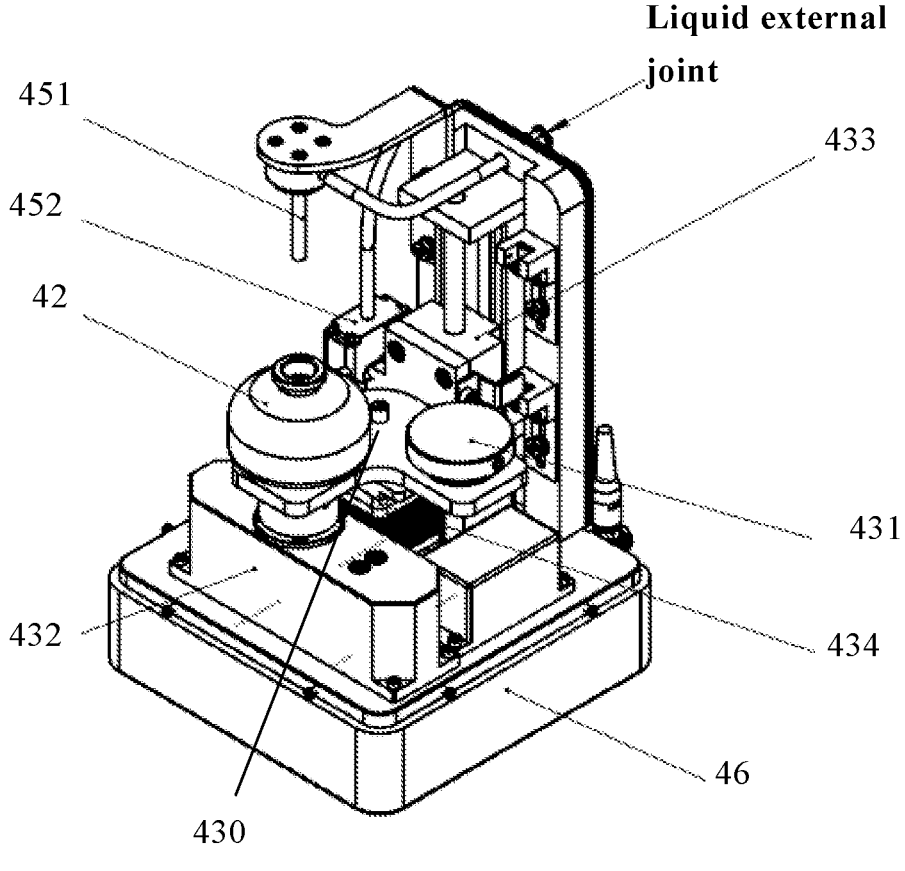
FIG. 3 is a schematic diagram of the three-dimensional structure of a flow rate feedback device according to an embodiment of the present invention.
Figure 4:
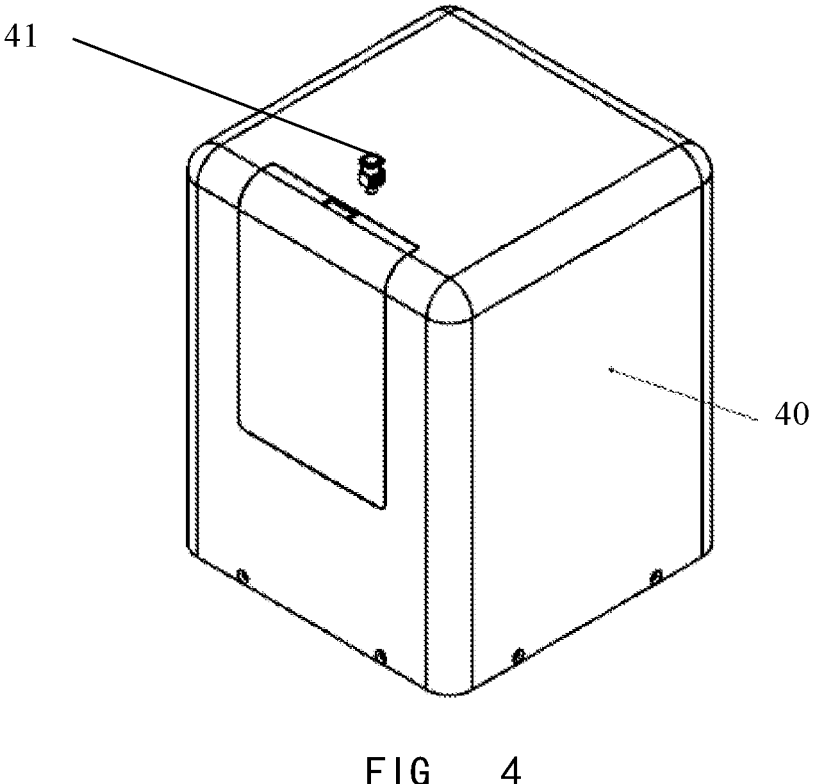
FIG. 4 is a three-dimensional structural diagram of the cover of the flow rate feedback device according to an embodiment of the present invention.
Figure 5:
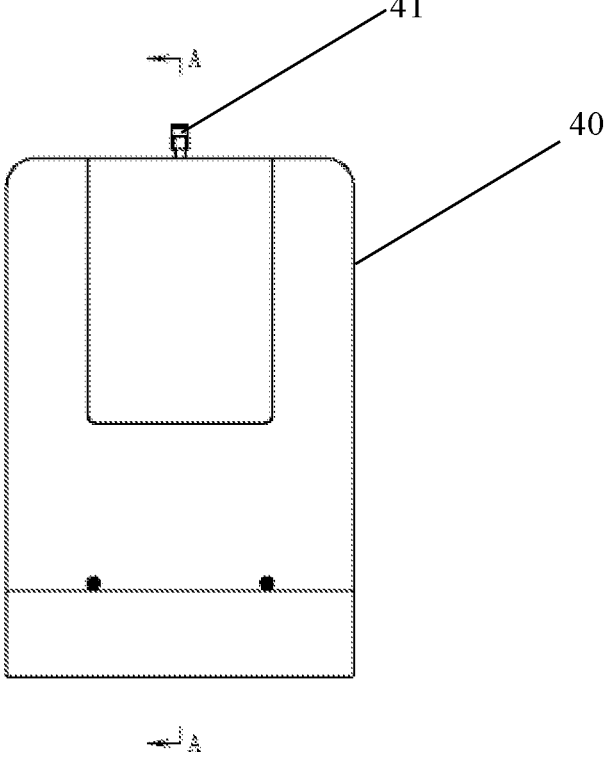
FIG. 5 is a cross section of a flow rate feedback device according to an embodiment of the present invention.

Referring to FIGS. 1-6, the present disclosure provides a microdialysis system comprising a flow rate feedback device, which comprises a perfusion device 1, a first connecting pipeline 2, a second connecting pipeline 3, and a flow rate feedback device 4.

The flow rate feedback device 4 includes a cover 40, a connecting needle 41, a liquid collection container 42, a calibration weighing module 43, a flow rate feedback control display module 44, and an automatic drainage mechanism 45. The specifications of the connecting needle 42 are selected according to the agreed liquid flow rate range.

Wherein the perfusion device 1 includes a micropump and a syringe, the micropump pumps the dialyzable substances through the syringe to the first connecting pipeline 2. One end of the first connecting pipeline 2 is fluidly connected to the syringe, the other end of the first connecting pipeline 2 is fluidly connected to the inlet of the microdialysis probe. The first connecting pipeline 2 is configured to transport the dialyzable substances to the microdialysis probe, so that the dialyzable substances enter the living organism through the microdialysis probe. The second connecting pipeline 3 is configured to transport dialysate from living organisms to the flow rate feedback device 4. One end of the second connecting pipeline 3 is fluidly connected to the outlet of the microdialysis probe, and the other end of the second connecting pipeline 3 is fluidly connected to the connecting needle 41.

The liquid collection container 42 is provided below the connecting needle 41 and is configured to collect dialysis fluid from living organisms. The calibration weighing module 43 is configured to regularly measure the weight of the liquid in the liquid collection container 42 according to the conditions and programs set in the flow rate feedback control display module 44, and transmit the measured liquid weighing value to the flow rate feedback control display module 44.

The flow rate feedback control display module 44 calculates a difference between the current liquid weighing value and the previous liquid weighing value to obtain a weighing sampling difference and compares it with the predetermined value to monitor whether the connecting needle 41 is discharging liquid normally, and then gives a feedback on the status of the flow rate of the liquid in the first connecting pipeline 2 and the second connecting pipeline 3.

In this embodiment, the calibration weighing module 43 comprises a stage 430, a pressure sensor 432, a lifting mechanism 433, and a rotating motor 434. The flow rate feedback control display module 44 comprises a signal processor and a controller.

The liquid collection container 42 comprises a mouth and a body. In order to avoid the volatilization of the collected liquid and make the weighing more accurate, the diameter of the mouth is configured to be much smaller than the diameter of the body. The bottom of the body is provided with a collection container annular projection that matches the calibration weighing module.

The pressure sensor 432 is provided below the stage 430, and a scale is connected to the pressure sensor 432, which includes the scale head. The function of the collection container annular projection is to fix it on the stage and to align the scale with the collection container annular projection to stably carry the liquid collection container.

The stage 430 includes a first section and a second section, with a liquid collection container 42 provided on the first section and customized weights provided on the second section. In this embodiment, the stage 430 is L-shaped. In an embodiment, when the calibration weighing module 43 performs weighing, the pressure sensor 432 is located directly below the first section of the stage 430; when the calibration weighing module 43 performs calibrating, the pressure sensor 432 is located directly below the second section of the stage 430. That is when the calibration weighing module 43 is automatically calibrating, the liquid collection container 42 is separated from the scale, and the customized weight 431 is connected to the scale. When the calibration weighing module 43 performs weighing, the customized weight 431 is separated from the scale, and the liquid collection container 42 is connected to the scale.

In this embodiment, the first section of the stage 430 is provided with a first through hole. The collection container annular projection passes through the first through hole and there is a certain gap between the collection container annular projection and the first through hole. In other words, the outer diameter of the collection container annular projection is smaller than the diameter of the first through hole. In addition, the collection container annular projection matches the scale head, so that when the calibration weighing module 43 is weighing, the scale head is embedded in the collection container annular projection without contact with the first through hole, or the collection container annular projection is embedded in the scale head without contact with the first through hole, that is, the scale only supports the liquid collection container 42, and then the pressure sensor weighs the liquid collection container 42. The second section is provided with a second through hole, and the bottom of customized weight 431 is provided with a weight annular projection. The weight annular projection passes through the second through hole and there is a certain gap between the weight annular projection and the second through hole. In other words, the outer diameter of the weight annular projection is smaller than the diameter of the second through hole. In addition, the weight annular projection matches the scale head, so that when the calibration weighing module 43 is calibrating, the scale head is embedded in the weight annular projection without contact with the second through hole, or the weight annular projection is embedded in the scale head without contact with the second through hole, that is, the scale only supports the customized weight 431 to complete calibration.

The lifting mechanism 433 comprises a lifting motor and a lead screw. The lifting mechanism 433 drives the stage 430 to move away from or close to the pressure sensor 432 in a vertical direction. The lead screw is connected to the stage 430, and the lifting motor is connected to the lead screw.

The rotating motor 434, in conjunction with the lifting mechanism 433, can switch between the liquid collection container and the customized weight 431 on the pressure sensor, achieving the weighing of the liquid in the liquid collection container and calibration with the customized weight 431. The rotating motor is connected to the stage 430, and the rotating motor 434 is used to drive the stage 430 to rotate in a horizontal plane.

Calibration weighing module 43 performs automatic calibration before weighing the dialysate collected in liquid collection container 42. The calibration weighing module is used to calibrate the weighing module before entering the weighing program based on the conditions and procedures set in the flow rate feedback control display module 44. In one embodiment, the calibration weighing module can set an interval for timed weighing based on the flow rate. In one embodiment, the weighing accuracy of the calibration weighing module is within the range of ±0.003 g.

In this embodiment, the calibration process only needs to be carried out at the beginning of each day. When the calibration weighing module 43 is calibrating, the lifting mechanism 433 lifts the liquid collection container 42 away from the scale head in a vertical direction, and then the rotating motor 434 rotates the stage 430, so that the second section of the stage 430 is provided above the pressure sensor 432. The flow rate feedback control display module 44 makes the pressure sensor 432 automatically reset to zero, next, the lifting mechanism 433 lowers the stage 430 in a vertical direction to the point where the scale head is embedded in weight annular projection of the customized weight 431, i.e. the scale holds the customized weight 431. The pressure sensor transmits the measured signal to the flow rate feedback control display module 44, which completes calibration according to internal instructions.

In other words, when the stage is raised and the scale is empty, the flow rate feedback control display module will make the pressure sensor automatically reset to zero. When the stage is lowered, the scale is embedded in the weight annular projection of the customized weight 431 to support the weight. At this time, the through hole of the stage forms a completely separated gap with the scale and the bottom of the weight. The flow rate feedback control display module will read the processed data of the pressure sensor signal, and complete calibration according to internal instructions.

When completing the calibration, the calibration weighing module 43 performs weighing. The lifting mechanism 433 lifts the stage 430 in the vertical direction, causing the customized weight 431 to detach from the scale head. Then, the rotating motor 434 rotates the stage 430, so that the first section of the stage 430 is located above the pressure sensor 432. The flow rate feedback control display module 44 automatically zeros the pressure sensor 432, next, the lifting mechanism 434 lowers the stage 430 in a vertical direction to the point where the scale head is embedded in the collection container annular projection, which means the scale supports the liquid collection container. The pressure sensor transmits the measured signal to the flow rate feedback control display module 44, and the measured signal is processed and displayed on the display screen of the flow rate feedback control display module 44.

In this embodiment, the calibration weighing module also includes a pressure sensor, which performs weighing through a connected scale. When the stage is raised and the scale is empty, the flow rate feedback control display module will make the pressure sensor automatically reset to zero. When the stage is lowered, the scale is embedded in the liquid collection container annular projection to support the liquid collection container, and the first through hole of stage forms a completely separated gap with the bottom of the scale and liquid collection container. At this time, the flow rate feedback control display module will process the signal of the pressure sensor and the corresponding data is displayed on the display screen.

In this embodiment, the signal processor is configured to receive signal data from the pressure sensor, process the received signal data, and then the corresponding data is displayed on the display screen. It should be noted that the signal processor simultaneously receives commands from the controller and executes various commands such as clearing (reset to zero), calibrating, and reading pressure sensor signals. The controller is used to control the actions of various components of the flow rate feedback device, such as controlling the actions of the lifting mechanism and the rotating motor in the calibration weighing module.

The automatic drainage mechanism 45 is used to discharge the liquid in the liquid collection container 42. The automatic drainage mechanism 45 includes a drain pipe 451 and a drain pump 452. When the weighing value of the liquid in the liquid collection container 42 reaches the maximum preset threshold, the flow rate feedback control display module 44 will make the lifting mechanism 433 and the rotating motor 434 cooperate to insert the drain pipe 451 into the liquid collection container 42, and start the drain pump 452 to discharge the liquid in the liquid collection container 42. In this embodiment, there further comprises a drain pipeline, which passes through the cover to form a liquid external joint.

In order to further prevent external air from entering the liquid collection container 42 and affecting the accuracy of the calibration weighing module, the connecting needle 44 is provided on the cover 40 and connected to the outlet of the second connecting pipe. The liquid collection container 42, calibration weighing module 43, and automatic drainage mechanism 45 are all provided inside the cover 40. Preferably, in order to achieve a compact structure of the flow rate feedback device 4, the automatic drainage mechanism 45 is arranged adjacent to the lifting mechanism 433.

The flow rate feedback device 4 also includes a base 46. The liquid collection container 42, the calibration weighing module 43, and the automatic drainage mechanism 45 are provided above the base 46. In order to achieve a more compact structure of the flow rate feedback device, the signal processor and controller are provided in the base 5 located below the stage.

It should be noted that in the present disclosure, the automatic drainage mechanism 45 and the calibration weighing module 43 can operate independently. When the time gap between the end of the current weighing and the start of the next weighing is sufficient for automatic liquid discharge, the automatic liquid discharge can be executed immediately during the intermittent weighing execution process once the liquid accumulation reaches the limit value. If the time gap between the two weighing actions is not enough for liquid discharge, the weighing will be paused for a while, and will continue after the liquid discharge is completed.

The flow rate feedback control display module can set parameters and control actions for the calibration weighing module 43 and the automatic drainage mechanism. The flow rate feedback display module also includes a display screen, which is used to display the current liquid weighing value and weighing sampling difference for real-time monitoring of liquid weight changes by users. Therefore, users can view the flow trend chart of the micro-flow pipeline in real-time through the monitoring screen to determine the relative stable state of the pipeline.

In this embodiment, the flow rate feedback control display module 44 of the flow rate feedback device 4 may also include an alarm module. When the weighing sampling difference is not equal to a preset value, the alarm module sends an alarm signal to the user.

Operating Instructions for Calibrating the Weighing Module:

This system is fully automatic during the use of the device. As long as the communication line is connected to the host and the liquid effluent collection is connected to the micro-flow pipeline, it can be started and operated in the device control.

Method for Determining the Flow Rate by Calibrating the Real-Time Data of the Weighing Module When the device was just running, due to the rapid advance of the micropump, the pressure inside the syringe and the tube was relatively high. It takes about 15-30 minutes for the flow rate to stabilize after releasing the excessive internal pressure.

So generally, we observe the changes in [weighing sampling difference] after 15 minutes.

For example, assuming that the liquid in the tube is pure water with a density of 1.0, it is necessary to measure the flow rate of a single pump. When we set the flow rate of the pump to 5 ul/min, we can observe the [weighing sampling difference] in a stable state, because the program is fixed to automatic weighing every 2 minutes. The weighing error of the weighing system is the highest±0.003 g, so the water output every two minutes should be 0.010±0.003 g. Although there are errors in the weighing system, liquid collection is based on the principle of droplet self-weight, which means that each droplet should be of the same weight in the same environment. Therefore, as long as the data changes within the range of 0.010±0.003 g every time, it indicates that the flow rate is stable.

Of course, a more accurate measurement of flow rate requires a longer period of time to calculate the average flow rate based on the total water output/time over an hour or several hours.

In this way, when the flow rate is needed to be adjusted slightly, we can slowly adjust the flow rate in the smallest pulse unit.

Characteristics of Calibration Weighing Module (1) The liquid collection method is novel and unique, and the structure of the liquid collection container is unique.

(2) According to the discharge volume, continuous working hours are required, and a range of 0.000 g to 199.999 g can be met.

(3) The interval time for automatic weighing can be freely set within the range of 10 seconds to 999 seconds based on the intermittent duration of liquid discharge.

(4) After startup, the system can automatically perform calibration with weights.

(5) Perform automatic zeroing before each weighing.

(6) The maximum weighing accuracy is ±0.003 g, and the relative standard deviation (RSD) is <0.01%.

(7) Supported external communication: ModbusTCP or ModbusRTU computer connection: RS485 serial port or Ethernet interface (for user software).

*Note: Requirements for measurement conditions: the wind speed of the weighing department is below 0.1 m/s, the indoor temperature variation range cannot exceed 0.2° C. for 15 minutes, the natural volatilization of liquid with constant humidity can be measured, and there is no abnormal vibration interference, static electricity interference, or electromagnetic interference.

The Microdialysis System Comprising the Flow Rate Feedback Device have One of the Following Functional Features:

(a) The present disclosure utilizes the principle that the amount of liquid pumped under normal conditions will inevitably discharge an equal amount of liquid in the microdialysis technology, and a flow rate feedback device is provided at the end of the pipeline, and the liquid collection container of the flow rate feedback device is regularly weighed and measured; once there is a sudden change in the regular trend of weighing data, an alarm will be triggered immediately. Based on this, the following faults can be analyzed and judged: (1) whether the probe or connecting pipeline is blocked; (2) whether the pipeline is leaking liquid or air; (3) whether the syringe is not provided properly;

(b) The present disclosure performs operational statistics on weighing data, and in special environments, problems can be discovered through pre-inspection, and new variables or coefficients can be added to make the weighing results more accurate;

(c) The calibration weighing module of the flow rate feedback device of the microdialysis system of the present disclosure can achieve calibration before weighing, and the flow rate feedback device integrates an automatic drainage mechanism, which means that after the device is turned on, there is no need for personnel to open the shell (cover) for any calibration or liquid accumulation work, and the device can work in a continuous closed state to ensure no interference and less volatilization to improve accuracy;

(d) Operate and run through a computer or human-machine dialogue interface; the computer or human-machine dialogue operation interface displays the following operating status of the device: standby, automatic calibration, in operation, and abnormal alarm;

The communication status between the device and the upper computer displayed in the computer or human-machine dialogue operation interface: normal or abnormal;

(e) Supporting user software, parameters can be changed, and data can be saved.

Other Technical Parameters of the Microdialysis System Including Flow Rate Feedback Device:

Liquid collection container: quantity 1, material can be designed and customized according to requirements (for those who need to continuously collect accumulated liquid for a long time, automatic discharge function can be used. Further, the liquid can be automatically discharged to the outside of the machine after reaching a certain amount);

Weights: quantity 1, made of stainless steel, with customizable weight;

Working temperature: 10-35° C.;

Motor: stepping motor system;

Voltage: DC24V;

Power consumption: maximum 50 W;

Size: 120×120×180 mm (length×width×height);

Weight: approximately 2 KG.

The Main Advantages of the Present Disclosure (a) The microdialysis system comprising a flow rate feedback device of the present disclosure can monitor that the micro-flow pipeline may have problems such as liquid blockage caused by the adsorption of detection substances or particle blockage, or detachment of individual joints when left unattended during long-term experiments;

(b) The microdialysis system comprising a flow rate feedback device of the present disclosure follows the principle that under normal conditions, the amount of liquid pumped will inevitably discharge an equal amount of liquid in the microdialysis technology, and a flow rate feedback device is provided at the end of the pipeline, and the liquid in the liquid collection container is regularly weighed and measured; once there is a sudden change in the weighing data, an alarm will be triggered immediately. Based on this, the following faults can be analyzed and judged: (1) whether the probe or connecting pipeline is blocked; (2) whether the pipeline is leaking liquid or air; (3) whether the syringe is not provided properly;

(c) The flow rate feedback device of the present disclosure has a compact and simple structure, and can view the flow trend chart of the micro-flow pipeline through the monitoring screen to determine the relative stable state of the pipeline;

(d) The weighing calibration module in the flow rate feedback device of the present disclosure can achieve high-precision weighing, and the flow rate feedback device covers its liquid collection container, calibration weighing module, etc. through a cover to prevent interference from external air, and also avoids the evaporation of liquid in the liquid collection container, thereby improving the weighing accuracy;

(e) The connecting needle, liquid collection container, calibration weighing module, signal processor and controller of flow rate feedback control display module, and automatic drainage mechanism of the flow rate feedback device of the present invention are integrated into the cover, thereby making the flow rate feedback device of the present invention compact in structure, small in space and volume, and easy to place and use.

All documents mentioned in the present invention is considered to be included as a whole in the disclosed content of this application, so as to serve as a basis for modification if necessary. In addition, it should be understood that after reading the above disclosed content of the present invention, those skilled in the art can make various changes or modifications to this application, and these equivalent forms also fall within the scope of protection claimed by this application.

What is claimed is:

1. A microdialysis system comprising a flow rate feedback device, wherein the system comprises:

a perfusion device (1), a first connecting pipeline (2), a second connecting pipeline (3), and the flow rate feedback device (4); the flow rate feedback device (4) comprising a connecting needle (41), a liquid collection container (42), a calibration weighing module (43), and a flow rate feedback control display module (44);

wherein the perfusion device (1) comprises a micropump and a syringe, and the micropump pumps dialyzable substances into the first connecting pipeline (2) through the syringe;

one end of the first connecting pipeline (2) is fluidly connected to the syringe, and the other end of the first connecting pipeline (2) is fluidly connected to an inlet of a microdialysis probe, the first connecting pipeline (2) is configured to transport dialyzable substances to the microdialysis probe, so that the dialyzable substances enter a living organism through the microdialysis probe;

the second connecting pipeline (3) is configured to transport dialysate from the living organism to the flow rate feedback device (4), one end of the second connecting pipeline (3) is fluidly connected to an outlet of the microdialysis probe, and the other end of the second connecting pipeline (3) is fluidly connected to the connecting needle (41);

the liquid collection container (42) is provided below the connecting needle (41) and configured to collect dialysate from the living organism;

the calibration weighing module (43) is configured to regularly measure weight of a liquid in the liquid collection container (42) according to conditions and programs set in the flow rate feedback control display module (44), and transmit a measured liquid weighing value to the flow rate feedback control display module (44); and the flow rate feedback control display module (44) performs a difference operation between a current liquid weighing value and a previous liquid weighing value to obtain a weighing sampling difference, and compares the weighing sampling difference with a predetermined value to monitor whether the connecting needle (41) is discharging liquid normally, and thus gives a feedback on a state of flow rate of the liquid in the first connecting pipeline (2) and the second connecting pipeline (3).

2. The microdialysis system according to claim 1, wherein the calibration weighing module (43) comprises a stage (430), which comprises a first section and a second section, the liquid collection container (42) being provided on the first section, and a customized weight (431) being provided on the second section.

3. The microdialysis system according to claim 2, wherein the calibration weighing module (43) further comprises a pressure sensor (432), which is provided below the stage (430).

4. The microdialysis system according to claim 3, wherein the calibration weighing module (43) further comprises a lifting mechanism (433), which comprises a lifting motor and a lead screw, the lifting mechanism driving the stage (430) to move in a vertical direction away from or close to the pressure sensor (432).

5. The microdialysis system according to claim 3, wherein the calibration weighing module (43) further comprises a rotating motor (434), which is connected to the stage (430), and the rotating motor (434) is configured to drive the stage (430) to rotate in a horizontal plane.

6. The microdialysis system according to claim 3, wherein a scale is connected to the pressure sensor (432), and the scale comprises a scale head;

the first section of the stage (430) is provided with a first through hole, and a bottom of the liquid collection container (42) is provided with a collection container annular projection, the collection container annular projection passing through the first through hole and there being a gap between the collection container annular projection and the first through hole, when the calibration weighing module (43) performs weighing, the scale head is embedded in the collection container annular projection.

7. The microdialysis system according to claim 6, wherein the second section is provided with a second through hole, and a bottom of the customized weight (431) is provided with a weight annular projection, the weight annular projection passing through the second through hole and there being a certain gap between the weight annular projection and the second through hole, when the calibration weighing module (43) performs calibrating, the scale head is embedded in the weight annular projection.

8. The microdialysis system according to claim 1, wherein the flow rate feedback device (4) further comprises a cover (45), wherein the connecting needle (44) is provided on the cover (45), and the liquid collection container (42) and calibration weighing module (43) are provided inside the cover (45).

9. The microdialysis system according to claim 1, wherein the flow rate feedback device (4) further comprises an automatic drainage mechanism (45), and the automatic drainage mechanism flow rate feedback device (4) is used to discharge a liquid in the liquid collection container (42).

10. The microdialysis system according to claim 9, wherein the flow rate feedback device (4) further comprises a base (46), wherein the liquid collection container (42), the calibration weighing module (43), and the automatic drainage mechanism (45) are provided above the base (46).

\* \* \* \* \*